(12) United States Patent
Morizumi

(10) Patent No.: US 11,104,347 B1
(45) Date of Patent: Aug. 31, 2021

(54) SYSTEM AND METHOD FOR MANAGING SHARED VEHICLES

(71) Applicant: ASAHI KASEI KABUSHIKI KAISHA, Tokyo (JP)

(72) Inventor: Masahiro Morizumi, Menlo Park, CA (US)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/920,330

(22) Filed: Jul. 2, 2020

(51) Int. Cl.
B60W 40/08 (2012.01)
G08G 1/00 (2006.01)
G07C 5/00 (2006.01)
A61L 9/00 (2006.01)
G16H 50/80 (2018.01)
B60H 3/00 (2006.01)

(52) U.S. Cl.
CPC ............ *B60W 40/08* (2013.01); *A61L 9/00* (2013.01); *B60H 3/00* (2013.01); *G07C 5/008* (2013.01); *G08G 1/202* (2013.01); *G16H 50/80* (2018.01); B60W 2540/01 (2020.02); B60W 2540/221 (2020.02)

(58) Field of Classification Search
CPC .......... B60W 40/08; B60W 2540/221; B60W 2540/01; B60W 2540/21; B60W 2540/041; B60W 2756/10; B60W 2420/10; B60W 2420/54; G08G 1/202; A61L 9/00; G07C 5/008; B60H 3/00; G16H 50/80; G16H 50/00; G16H 50/30; A61B 5/08; A61B 5/0816; A61B 5/08263; A61B 5/72; A61B 5/7271; A61B 5/7275; A61B 5/7282; A61B 5/74
See application file for complete search history.

(56) References Cited

U.S. PATENT DOCUMENTS

| | | |
|---|---|---|
| 7,177,738 B2 | 2/2007 | Diaz |
| 10,219,750 B2 | 3/2019 | Duan et al. |
| 2015/0348179 A1 | 12/2015 | Kamisawa |
| 2017/0086778 A1 | 3/2017 | Cahan et al. |

(Continued)

FOREIGN PATENT DOCUMENTS

| | | |
|---|---|---|
| JP | 2011140271 A | 7/2011 |
| JP | 2012173862 A | 9/2012 |

(Continued)

Primary Examiner — Ryan W Sherwin
(74) Attorney, Agent, or Firm — Kenja IP Law PC

(57) ABSTRACT

A system for managing shared vehicles comprises an acoustic event detector including an acoustic sensor for detecting an acoustic event in a compartment of a vehicle, a vehicle terminal electrically connected to the acoustic event detector, and an external server communicating with the vehicle terminal via a network. At least one of the vehicle terminal and the external server comprises a processor. The processor is configured to implement the steps of extracting a respiratory disease symptom of a passenger in the vehicle from the detected acoustic event, assessing the respiratory disease symptom of the passenger to generate infection risk information associated with an infection risk of a next passenger expected to ride the vehicle, and transmitting the infection risk information to an external user terminal via the network. A method for managing shared vehicles is also provided.

19 Claims, 8 Drawing Sheets

(56) References Cited

U.S. PATENT DOCUMENTS

| 2019/0133511 A1* | 5/2019 | Migneco .................. B60N 2/24 |
| --- | --- | --- |
| 2019/0148023 A1* | 5/2019 | Sadilek .................. G06N 20/00 |
| | | 705/2 |
| 2019/0237094 A1 | 8/2019 | Kakadiaris et al. |
| 2020/0360858 A1* | 11/2020 | Mathur ................ B01D 53/007 |

FOREIGN PATENT DOCUMENTS

| JP | 2018179547 A | 11/2018 |
| --- | --- | --- |
| WO | 2019003325 A1 | 1/2019 |

* cited by examiner

# SYSTEM AND METHOD FOR MANAGING SHARED VEHICLES

TECHNICAL FIELD

The present disclosure relates to a system and method for managing shared vehicles, in particular, rental/car sharing fleet.

BACKGROUND

For businesses involving a fleet of vehicles such as a vehicle rental service and a car sharing service, managing the condition of each vehicle is the key to maximize the usage of the fleet. For example, U.S. Pat. No. 7,177,738 proposes a vehicle management system that is capable of easily obtaining information on the condition and usage of a vehicle, thereby managing the fleet of vehicles with high efficiency and low cost.

These services, however, face a rapidly changing operating environment due to the new coronavirus disease (COVID-19). Both customers and service providers are likely to have significantly increased expectation of hygiene. The service providers need to reassure their customers that they have taken sufficient steps to ensure their safety.

The virus is thought to spread mainly from person-to-person through respiratory droplets produced when an infected person coughs, sneezes, or talks. The Centers for Disease Control and Prevention (CDC) has released guidelines to reduce the risk of exposure to the virus that causes COVID-19. The guidelines encourage the service providers to, at minimum, clean and disinfect frequently touched surfaces in the vehicle.

Recent studies also indicate that the virus can persist in fine particles know as aerosols and survive in the air for several hours. As the aerosols may infect cells throughout that time period, it is ideal to take more thorough cleaning and disinfection procedures if a passenger is suspected to contract the disease. It is, however, hard for the service providers to identify a risk of infection when the vehicle is returned.

SUMMARY

It is, therefore, an object of the present disclosure to provide a system and method for managing shared vehicles that is capable of remotely determine a health condition of a passenger of the vehicle, thereby ensuring the health safety of the next passenger.

In order to achieve the object, one aspect of the present disclosure is a system for managing shared vehicles, the system comprising:
an acoustic event detector including an acoustic sensor for detecting an acoustic event in a compartment of a vehicle,
a vehicle terminal electrically connected to the acoustic event detector, and
an external server communicating with the vehicle terminal via a network,
wherein at least one of the vehicle terminal and the external server comprises a processor, and
the processor is configured to implement the steps of:
extracting a respiratory disease symptom of a passenger in the vehicle from the detected acoustic event;
assessing the respiratory disease symptom of the passenger to generate infection risk information associated with an infection risk of a next passenger expected to ride the vehicle; and
transmitting the infection risk information to an external user terminal via the network.

As used herein, the term "vehicle" generally means every device in, upon, or by which any person is transported or drawn, and may be used upon fixed rails, tracks or the like, or in the air or on water. As such vehicle, a motor vehicle, a bus, a train, a cable car, a gondola lift, an amusement ride, an airplane, and a motorboat may be recited by way of example.

The vehicle terminal is a data processing device such as a general-purpose computer, a personal computer, a dedicated computer, a workstation, a PCS (Personal Communications System), a cellular (mobile) telephone, a smart phone, an RFID receiver, a laptop computer, a tablet computer and any other programmable data processing device.

The network is not limited to a particular communication network and may include any communication network including, for example, a mobile communication network and the internet.

The processor may be, but not limited to, a general-purpose processor or a dedicated processor specialized for a specific process. The processor includes a microprocessor, a central processing unit (CPU), an application specific integrated circuit (ASIC), a digital signal processor (DSP), a programmable logic device (PLD), a field programmable gate array (FPGA), a controller, a microcontroller, and any combination thereof.

The respiratory disease symptom includes, but is not limited to, cough, sneeze, breath, sniffle, throat clearing and the like.

In one embodiment, the system may additionally have a position detector such as a GPS (Global Positioning System) receiver for detecting a current position of the vehicle. In this case, the processor may be further configured to implement the step of obtaining at least one of environmental information around the vehicle and infection risk information from a neighboring vehicle via the network, and the step of assessing the respiratory disease of the passenger may be implemented also on the basis of the at least one of environmental information around the vehicle and infection risk information from a neighboring vehicle.

In another embodiment, the processor may be further configured to implement the step of modifying at least one of a communication frequency and information to be transmitted to the external server.

In a further embodiment, the system may also have an air cleaner in the vehicle, and the processor may be further configured to implement the step of controlling the air cleaner on the basis of a frequency of occurrence of the respiratory disease symptom. In addition or alternatively, the system may further have a biological information acquisition unit for acquiring biological information of the passenger, and the processor may be further configured to implement the step of controlling the biological information acquisition unit based on a frequency of occurrence of the respiratory disease symptom.

In yet another embodiment, the processor may be further configured to implement the steps of generating vehicle compartment contamination information indicating a necessity of a disinfectant procedure prior to a next use of the vehicle based on the infection risk information, and transmitting the vehicle compartment contamination information to the external user terminal via the network. In this embodiment, the external server may include a database storing reservation information and status information of the shared vehicles, and may modify the status information of the vehicle to reflect the vehicle compartment contamination information. When the vehicle compartment contamination information indicates that the disinfectant procedure is needed and the reservation information indicates that the vehicle has a reservation, the external server may search another available vehicle and assigns the available vehicle to the reservation. The vehicle compartment contamination information may be updated after the disinfectant procedure is completed so as to indicate that the vehicle is clean.

In a yet further embodiment, the external server may search a potentially contaminated vehicle having a usage history similar to that of the vehicle determined as high infection risk, and may modify at least one of a communication frequency and information to be transmitted to the external server.

Another aspect of the present disclosure is a method for managing shared vehicles, the method comprising the steps of:

detecting an acoustic event in a compartment of a vehicle;

extracting a respiratory disease symptom of a passenger in the vehicle from the detected acoustic event;

assessing the respiratory disease symptom of the passenger to generate infection risk information associated with an infection risk of a next passenger expected to ride the vehicle; and transmitting the infection risk information to an external user terminal via a network.

The method may further comprise the steps of:

detecting a current position of the vehicle; and obtaining at least one of environmental information around the vehicle and infection risk information from a neighboring vehicle via the network. In this case, the step of assessing the respiratory disease of the passenger may be implemented also on the basis of the at least one of environmental information around the vehicle and infection risk information from a neighboring vehicle.

The method may further comprise the steps of: modifying at least one of a communication frequency and information to be transmitted to the external server; controlling an air cleaner in the vehicle on the basis of a frequency of occurrence of the respiratory disease symptom; and/or acquiring biological information of the passenger on the basis of a frequency of occurrence of the respiratory disease symptom;

In another embodiment, the method may further comprise the steps of generating vehicle compartment contamination information indicating a necessity of a disinfectant procedure prior to a next use of the vehicle based on the infection risk information; and transmitting the vehicle compartment contamination information to the external user terminal via the network. In addition, the method may further comprise the steps of accessing a database storing reservation information and status information of the shared vehicles; and modifying the status information of the vehicle to reflect the vehicle compartment contamination information. Furthermore, the method may further comprise the step of, when the vehicle compartment contamination information indicates that the disinfectant procedure is needed and the reservation information indicates that the vehicle has a reservation, searching another available vehicle and assigns the available vehicle to the reservation. The method may further comprise the step of updating the vehicle compartment contamination information after the disinfectant procedure is completed so as to indicate that the vehicle is clean.

In a further embodiment, the method may further comprise the step of searching a potentially contaminated vehicle having a usage history similar to that of the vehicle determined as high infection risk, and modifying at least one of a communication frequency and information to be transmitted to the external server.

According to the system and method for managing shared vehicles, it is possible to remotely determine a health condition of a passenger or passengers of the vehicle, thereby ensuring the health safety of the next passenger.

These and other aspects may be understood more readily from the following description and the appended drawings.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION

Figure 1:
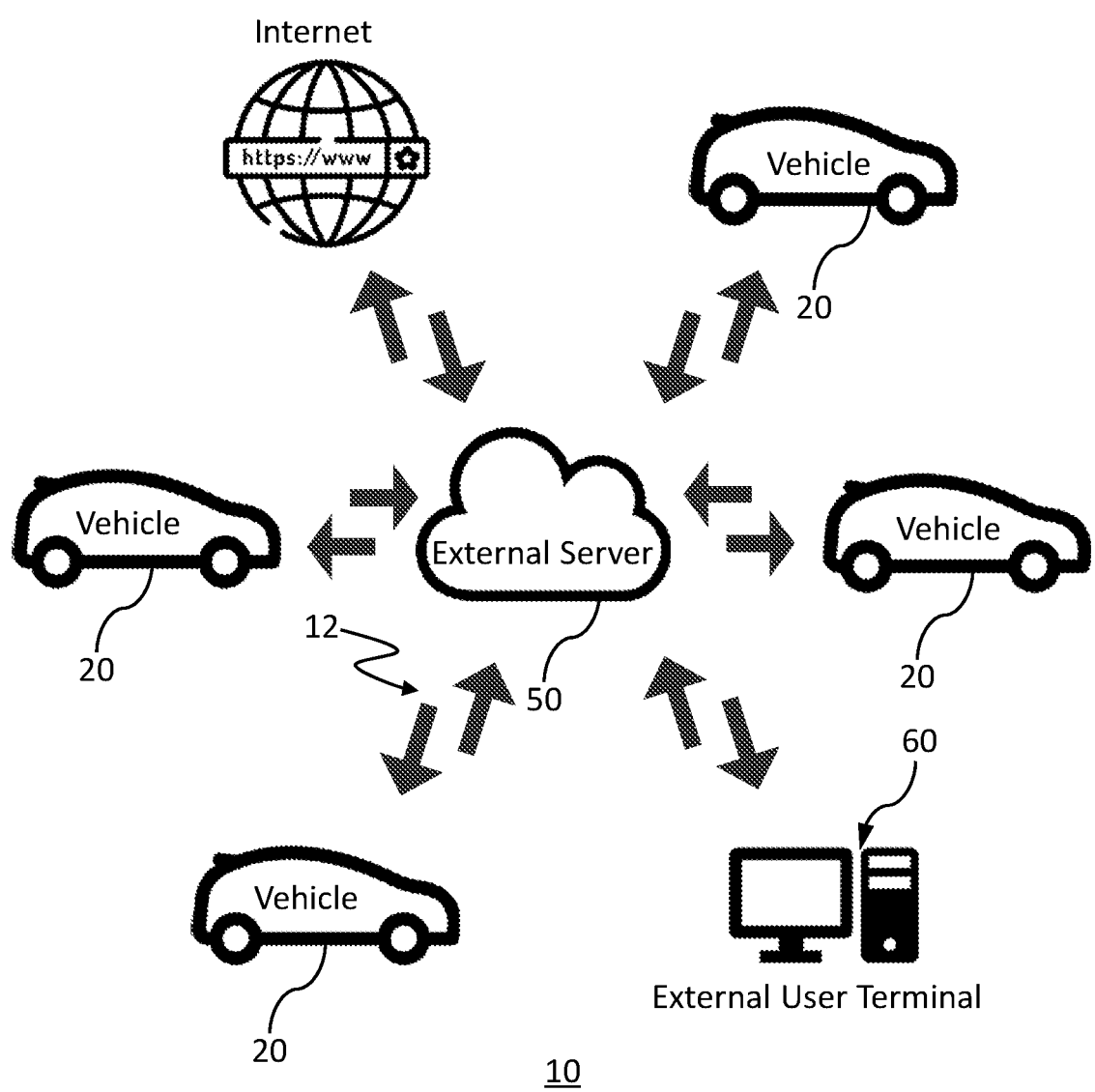
FIG. 1 is a schematic diagram of a system for managing shared vehicles according to an embodiment of the present disclosure.
Figure 2:
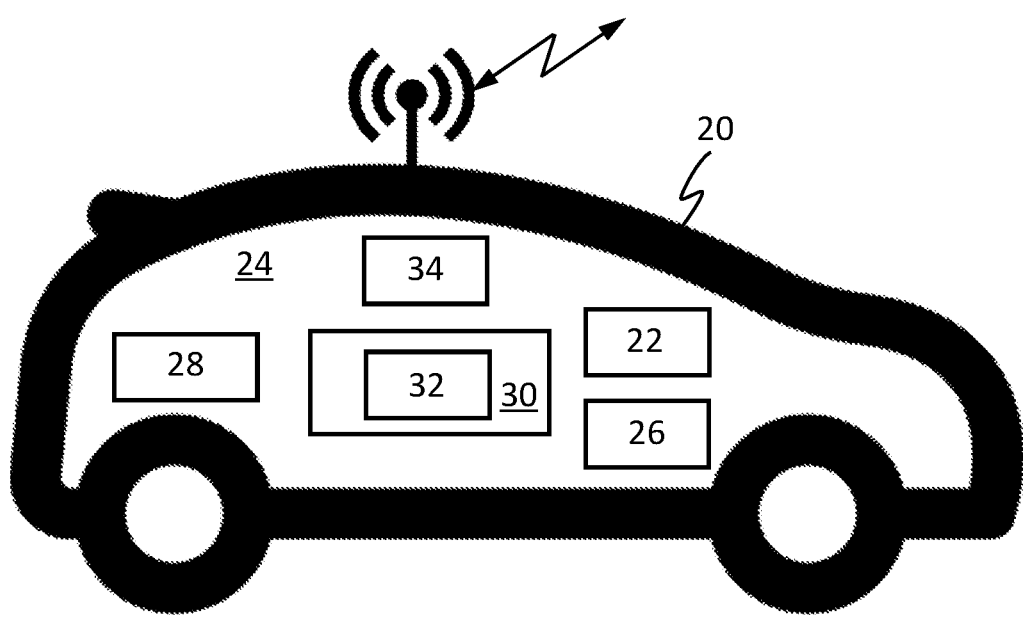
FIG. 2 is a schematic diagram of a part of the system mounted on a vehicle.

Embodiments will now be described with reference to the accompanying drawings. FIG. 1 is a schematic diagram of a schematic diagram of a system for managing shared vehicles according to an embodiment of the present disclosure, and FIG. 2 is a schematic diagram of a part of the system mounted on a vehicle.

A system 10 is designed for managing shared vehicles 20. Each vehicle 20 has an acoustic event detector 22 which includes an acoustic sensor for detecting an acoustic event in a compartment 24 of a vehicle 20. The acoustic sensor may be any type of a sensor, such as a microphone, that converts a sound signal (e.g., sound wave) into a voltage or current proportional to the detected signal. The acoustic sensor may include an electrostatic sensor or piezoelectric sensor (e.g., high frequency ultrasonic sound sensor) that detects sound pressure waves within the ultrasound range. More than one acoustic sensors may be used depending on, for example, the size, capacity and design of the compartment 24. The acoustic sensor may be dedicated to the system 10, but a microphone provided for another system such as a navigation system, a communication system, or an audio system may also be used. The acoustic sensor may be connected to the acoustic event detector 22 in a wired or wireless manner.

A cellular phone may also serve as the acoustic sensor via a wireless connection such as Bluetooth.

A vehicle terminal 30 is also provided in the vehicle 20 and electrically connected to the acoustic event detector 22. An external server 50 located at a remote site such as a data center communicates with the vehicle terminal 30 and an external user terminal 60 via a network 12.

The system 10 also has a processor 32 for processing and analyzing the acoustic event detected by the acoustic event detector 22. The processor 32 may be provided in the vehicle terminal 30, the external server 50 or both of them. In the embodiment shown in FIG. 2, the processor 32 is provided in the vehicle terminal 30. The vehicle 20 is also equipped with a biological information acquisition unit 26, an air cleaner 28, and a position detector 34, which will be discussed below. One or more sensors (not shown) may be provided for measuring the air quality, the temperature, the humidity and the like inside and/or outside the vehicle 20.

Figure 3:
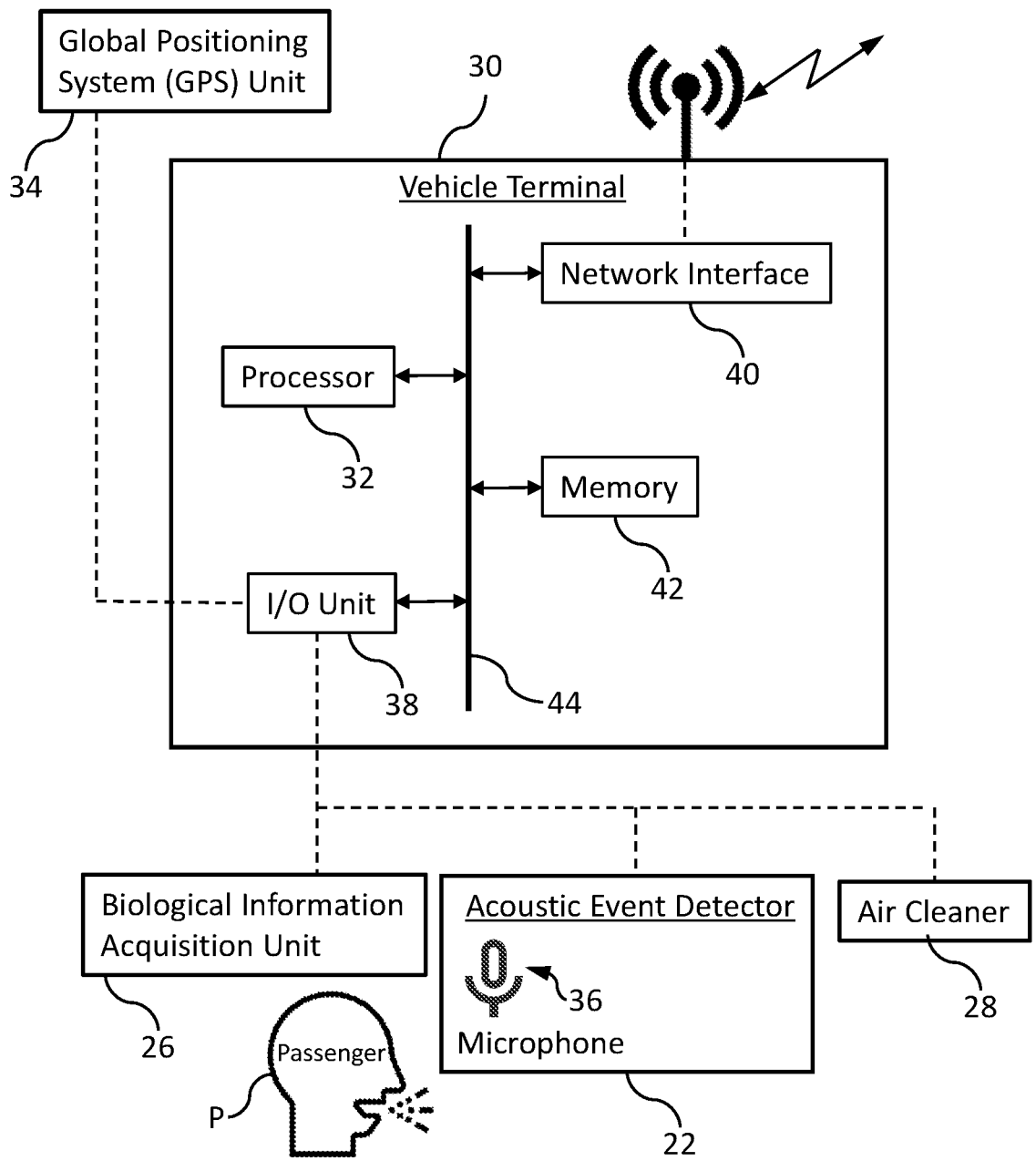
FIG. 3 is a block diagram showing the part of the system mounted on the vehicle.

FIG. 3 is a block diagram showing the part of the shared vehicles managing system 10 mounted on the vehicle 20. The acoustic event detector 22 has a microphone 36 as an acoustic sensor for capturing acoustic sounds and detecting an acoustic event produced by a passenger P in the compartment 24. The microphone 36 may be integrated in the acoustic event detector 22 itself, or may be a stand-alone type and coupled to the acoustic event detector 22 in a wired or wireless manner. In either event, the acoustic event detector 22 receives the captured acoustic sounds as electric signals from the microphone 36 and processes the electric signals, for example, by subjecting the electric signals to an analog-to-digital conversion to generate acoustic data.

The vehicle terminal 30 communicates with other units mounted in the vehicle 20, such as the acoustic event detector 22, the biological information acquisition unit 26, the air cleaner 28, and the position detector (GPS unit) 34 via an I/O (Input/Output) unit 38. The vehicle terminal 30 also communicates with the external server 50 via a network interface 40. The network interface may include a communication module compatible with mobile communication standards such as 4th Generation (4G) and 5th Generation (5G). The communication network may be an ad hoc network, a local area network (LAN), a metropolitan area network (MAN), a wireless personal area network (WPAN), a public switched telephone network (PSTN), a terrestrial wireless network, an optical network, or any combination thereof. The vehicle terminal 30 also includes a memory 42 which may function as, for example, a main storage device, a supplemental storage device, or a cache memory. The memory 42 stores any information used for the operation of the vehicle terminal 30. For example, the memory 42 may store a system program, an application program, data from the other units, data to be sent to the external server 50, data acquired from the external server 50 and so on. The information stored in the memory 42 may be updatable by, for example, information acquired from the external server 50 by the network interface 40. The memory 42 may be, for example, a semiconductor memory, a magnetic memory, or an optical memory. The memory 42 is not particularly limited to these, and may include any of long-term storage, short-term storage, volatile, non-volatile and other memories. Further, the number of memory modules serving as the memory 42 and the type of medium on which information is stored are not limited. The processor 32, the I/O unit 38, the network interface 40 and the memory 42 are electrically connected with each other via a bus 44.

Figure 4:
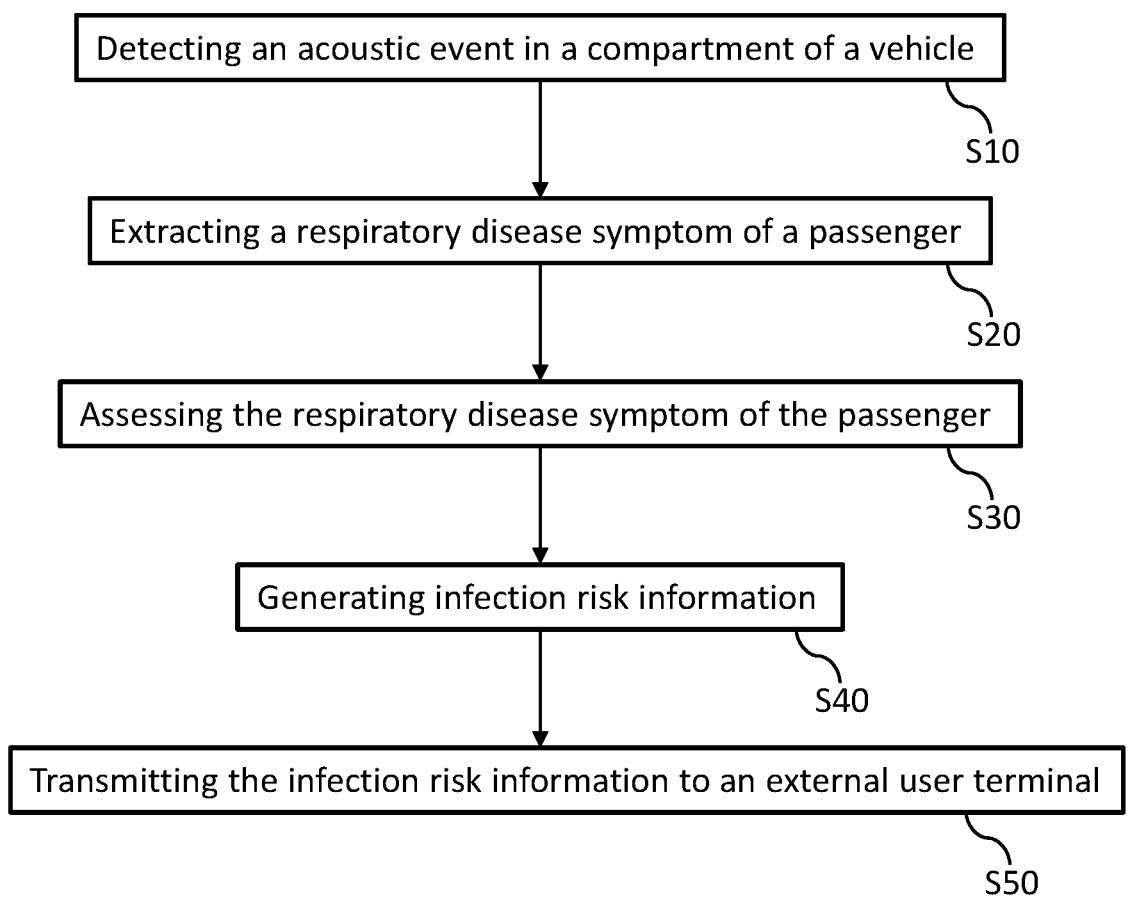
FIG. 4 is a flowchart showing steps implemented by the vehicle terminal according to another embodiment of the present disclosure.

Referring now to FIG. 4, the operation of the shared vehicles managing system 10 will be discussed.

At the step S10, the microphone 36 of the acoustic event detector 22 captures environmental sounds including sounds produced by the passenger P in the compartment 24 and converts the sound into the acoustic data. Then, the acoustic data is transferred to an I/O (input/output) unit 38 of the vehicle terminal 30.

The processor 32 extracts, at the step S20, a respiratory disease symptom of the passenger P from the acoustic data. For example, filtering or other types of frequency and/or amplitude analysis may be used to identify distinctive features of the captured acoustic data, or to remove extraneous (e.g., background) noise components from the acoustic data. The processor 32 further processes the distinctive features, for example, by comparing attributes of the features to a lookup table, database, or other data organization structure stored in the memory 42, thereby identifying the respiratory disease symptom. The respiratory disease symptom may include, for example, the coughing, the sneezing, the wheezing, the sniffing, the throat clearing, the nasally voice, the shallow breathes and the deep breathes. A model or algorithm used for extracting the respiratory disease symptom may be modified by the passenger's personal characteristics such as age, sex, race and anamnesis to enhance the accuracy of the extraction. Machine learning may be used to build and improve the model or algorithm. Alternatively, the model or algorithm may be updated via the network.

Then, at the step S30, the processor 32 assesses the respiratory disease symptom. For example, the intensity, frequency and duration of the coughing and/or the sneezing may be compared with the lookup table stored in the memory 42 to determine a severity of the symptom. A model or algorithm used for assessing the respiratory disease symptom may be modified by the passenger's personal characteristics such as age, sex, race and anamnesis to enhance the accuracy of the assessment. Machine learning may be used to build and improve the model or algorithm. Alternatively, the model or algorithm may be updated via the network.

At the step S40, the processor 32 generates infection risk information based on the severity of the symptom, and, optionally, other conditions of the vehicle. For example, the number of passengers, the size of the compartment, the air quality and the humidity and the temperature in the compartment may be weighed.

The processor 32 transmits, at the step S50, the infection risk information via the network interface 40 over the network to the external server 50. Other information such as a vehicle ID, the number of people having the symptom, and the location of the people having the symptom in the compartment (e.g., front passenger seat, driver seat and the like) may also be transmitted to the external server 50. The external server 50 forwards all or a part of the information to the external user terminal 60. The external user terminal 60 may be placed at, for example, a branch office of the service provider where the vehicle 20 is supposed to be returned. More than one external user terminal 60 are connected to the external server 50.

Figure 5:
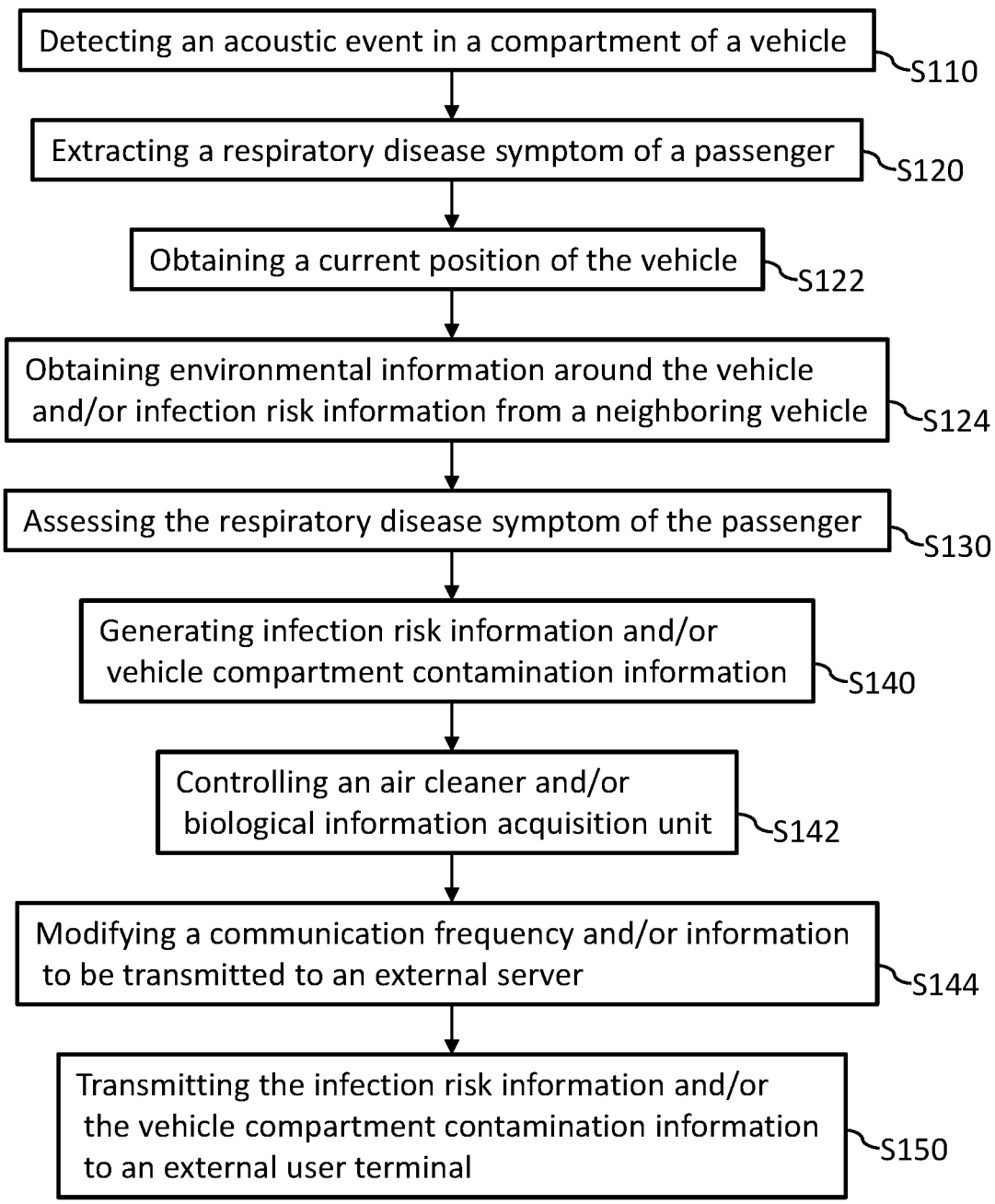
FIG. 5 is a flowchart showing steps implemented by the vehicle terminal according to another embodiment of the present disclosure.

FIG. 5 is a flowchart showing the steps implemented by the vehicle terminal according to another embodiment.

At the step S110, the acoustic event detector 22 captures the environmental sounds which are converted sound into the acoustic data and then transferred to the I/O unit 38. The processor 32 extracts, at the step S120, the respiratory disease symptom of the passenger P from the acoustic data. These steps may be implemented in the similar manner as the steps S10 and S20 discussed above.

Then, at the step S122, the processor 32 obtains a current position of the vehicle 20 from the GPS unit 34. The GPS unit 34 may be dedicated to the shared vehicle managing system 10, but a GPS unit provided for another system such as a navigation system also be used. A GPS unit integrated in a cellular or smart phone may also serve as the GPS unit 34 via a wireless connection such as Bluetooth.

At the step S124, the processor 32 generates a query including the current position of the vehicle 20 and transfers the query via the network interface 40 to the external server 50 or any other server on the internet. In response, environmental information around the vehicle 20 is sent back from the server. The environmental information may include the weather, the temperature, the humidity, the pressure, the wind velocity, the pollen counts, the air quality index (AQI), the particulate matter (PM) 2.5 and any other information associated with potential and known causes of respiratory diseases. In addition or alternative to the environmental information, the external server 50 searches a vehicle currently or recently driving in the same area (neighboring vehicle) and, if any, sends back the infection risk information obtained from the neighboring vehicle to the processor 32.

The processor 32 assesses, at the step S130, the respiratory disease symptom. In this embodiment, the information obtained via the network (i.e., the environmental information around the vehicle 20 and/or the infection risk information from the neighboring vehicle) is also taken into the assessment of the respiratory disease symptom. For example, when the pollen counts and/or the AQI is high, the processor 32 raise a risk threshold of the frequency of sneezing as there will be a high chance of sneezing due to the pollen or air pollution (i.e., sneezing not related to the respiratory diseases). The external server 50 may also calculate an average frequency of sneezing per person in that area on the bases of information accumulated from the vehicles managed by the external server 50 and send it back to the processor 32. The processor 32 may subtract the average frequency of sneezing from the measured frequency of sneezing of the passenger P and use the subtraction for the assessment.

At the step S140, the processor 32 generates infection risk information based on the severity of the symptom. In addition or as an alternative, contamination information of the vehicle compartment 24 may be generated. The concentration of aerosols (i.e., the level of contamination) in the compartment 24 of the vehicle 20 depends on not only the frequency of respiratory disease symptoms but also the size or capacity of the compartment 24 of the vehicle 20 as well as the duration of the symptoms. Therefore, the vehicle compartment contamination information should be determined with considering these factors as well. That is, the infection risk information indicates a likelihood (risk) of an infection of a next passenger expected to ride the vehicle, while the vehicle compartment contamination information indicates a necessity of a disinfectant procedure after the vehicle is returned and prior to a next use of the vehicle.

When a likelihood of contamination of the compartment is increasing, the processor 32 may activate (if not activated) or turn up (if already activated) the air cleaner 28 as a remediation action at the step S142. The air cleaner 28 may be equipped with at least one of a filtering device, which removes particles including pollen and PM 2.5 and microorganisms to purify the air, and a disinfecting device such as a UV lamp and an ozone generator, which kills or inactivates microorganism. The processor 32 may also activate a biological information acquisition unit 26 to collect additional information of the passenger and accurately determine the infection risk of the next passenger. The additional information collected by the biological information may include, for example, heart rate (HR), respiratory rate (RR), blood pressure (BP), body temperature (BT) and oxygen saturation ($SpO_2$).

The communication frequency between the processor 32 and the external server 50 and types of the information to be transmitted to the external server 50 may be modified at the step S144. For example, at a normal state, the communication frequency is set to be low in order to reduce the cost associated with the communication and/or loads of the vehicle terminal 30 and the external server 50. When the infection risk of the passenger P is higher, the communication frequency is set to be higher so that a health condition of the passenger can be tracked more frequently. In addition or as an alternative, the additional information collected by the biological information acquisition unit 26 may be integrated into the information to be transmitted to the external server 50 so that the health condition of the passenger can be evaluated more accurately.

Then, the processor 32 transmits, at the step S150, the infection risk information and/or the vehicle compartment contamination information via the network interface 40 over the network to the external server 50. The external server 50 forwards all or a part of the information to the external user terminal 60.

The external server 50 may utilize the information received from the processor 32 in various ways. For example, the external server 50 may accumulate the data from the vehicles over the time and monitor a clue of the outbreak of the respiratory disease and/or allergy. The external server 50 may also visualize the infection risk information from multiple vehicles on a map, and provide the map to drivers or send a warning to a vehicle driving within or toward an area where the infection risk is considered as high via the network. The information and the map may be provided to other service providers and governmental agencies such as the CDC.

Figure 6:
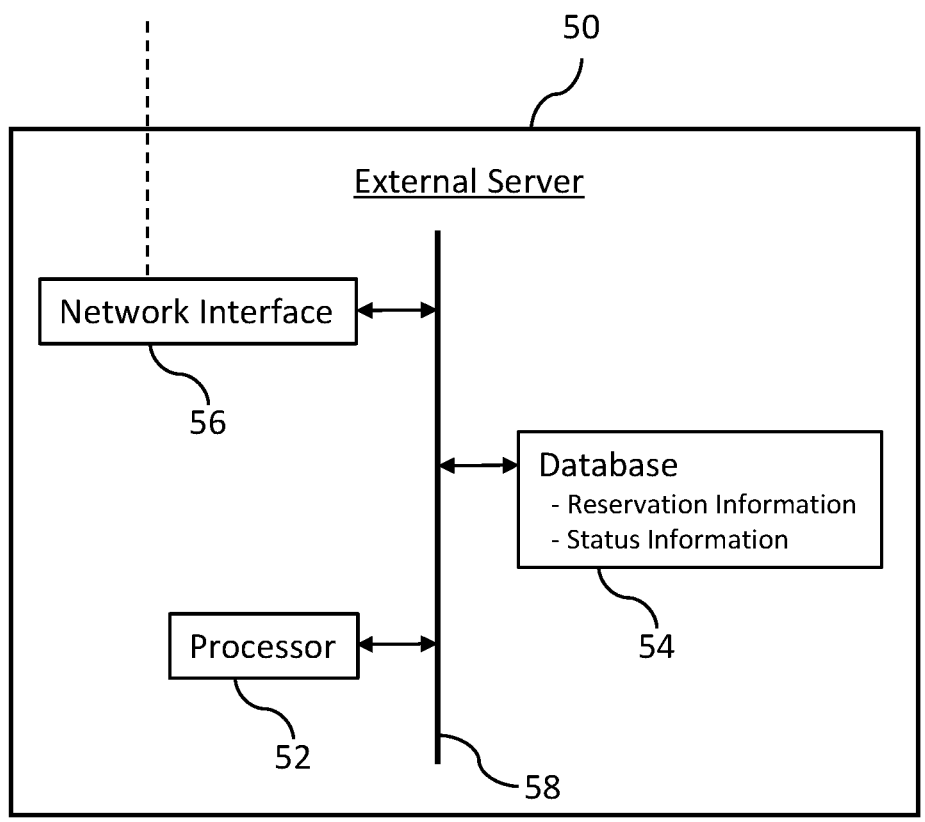
FIG. 6 is a block diagram showing an example of the external server used in the system for managing shared vehicles according to one embodiment of the present disclosure.

In one embodiment shown in FIG. 6, the external server 50 utilizes the information to manage an entire fleet schedule. The external server 50 includes a processor 52, a database 54 and a network interface 56 which are connected with each other via a bus 58. The database 54 stores reservation information and status information of the shared vehicles managed by the system 10.

Figure 7:
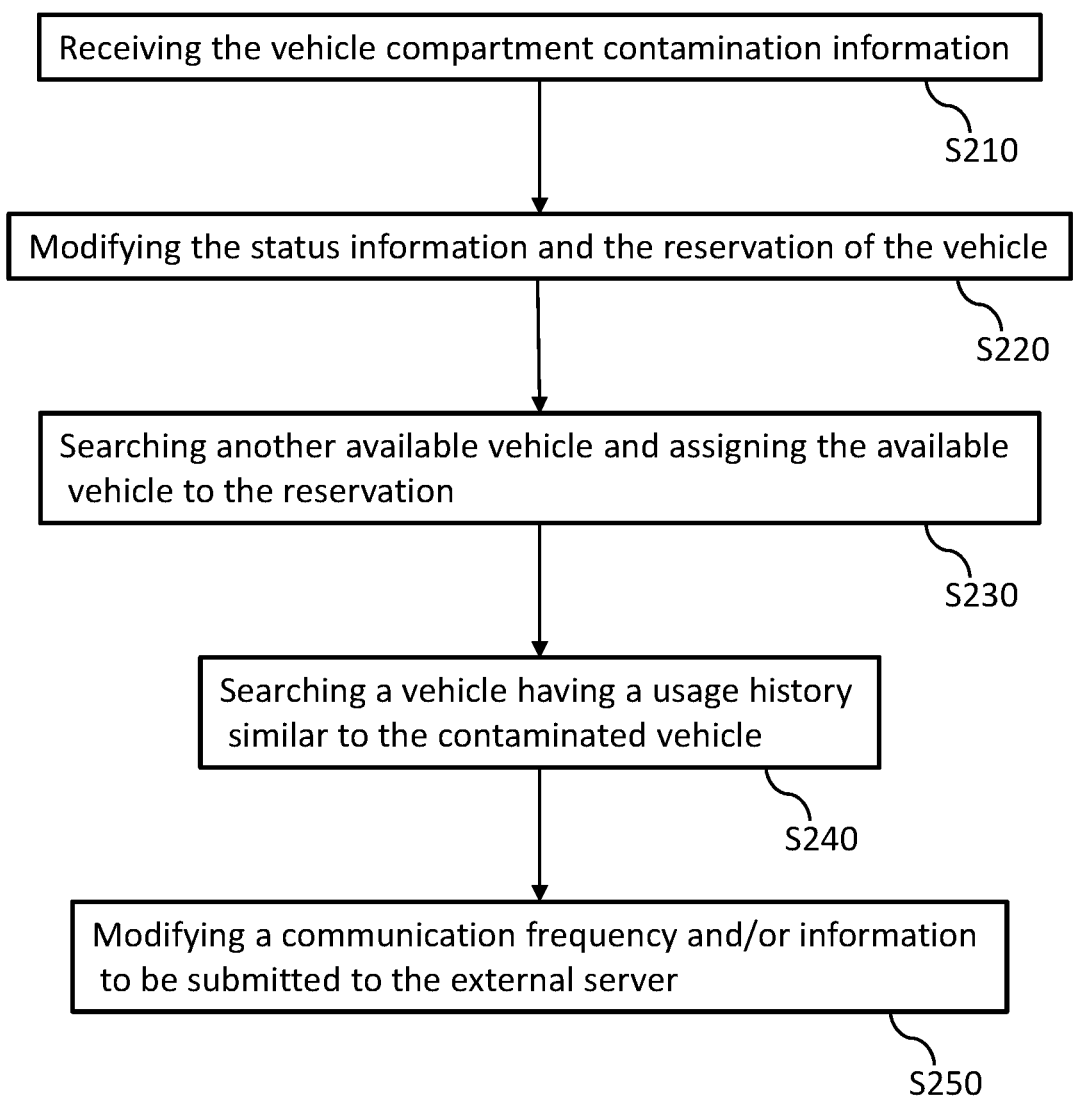
FIG. 7 is a flowchart showing steps implemented by the external server according to another embodiment of the present disclosure.
Figure 8:
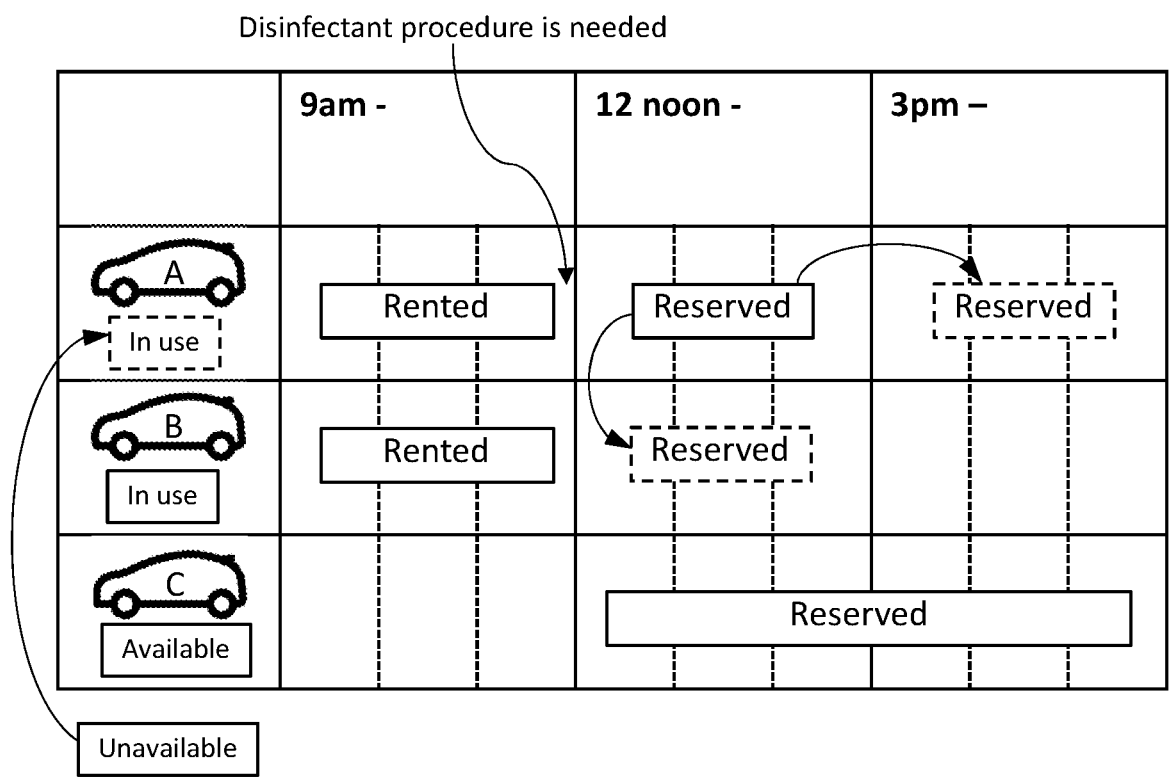
FIG. 8 is an example of status information and reservation information stored in a database.

Referring now to FIGS. 7 and 8, a procedure to manage the fleet schedule is discussed. FIG. 7 is a flowchart showing steps implemented by the external server and FIG. 8 is an example of the fleet schedule including the status information and the reservation information stored in the database 54. In this embodiment, the external server 50 is managing the schedules of vehicles A, B and C.

The processor 52 receives the vehicle compartment contamination information from the vehicle terminal 30 via the network interface 56 over the network (S210). Depending on the content of the vehicle compartment contamination information, the processor 52 modifies the status information of the vehicle 20 to reflect the vehicle compartment contamination information stored in the database 54 (S220). For example, when the vehicle compartment contamination information from the vehicle A indicates that the disinfectant procedure is needed, the processor 52 changes the status information of the vehicle A from "In use" to "Unavailable", which will prohibit any future reservations from being assigned to the vehicle A. Then, the processor 52 looks up the reservation information of the vehicle A. In this case, a reservation already exists in a time slot between 12 noon and 3 pm. Since the vehicle A needs to be disinfected prior to the next use and will be unavailable until the disinfectant procedure is completed, this reservation must be changed. Thus, the processor 52 searches an available vehicle in this time slot from the fleet schedule. As the vehicle B is available in this time slot, the processor 52 reassigns the reservation to the vehicle B and move the reservation information from the vehicle A to the vehicle B (S230). Alternatively, the processor 52 reschedule the reservation to another time slot (e.g., between 3 pm and 6 pm) to secure sufficient time to complete the disinfectant procedure. Upon receiving a report of a completion of the disinfectant procedure, the processor updates the vehicle compartment contamination information from "Unavailable" to "Available" so as to indicate that the vehicle is clean.

Optionally, the external server 50 may also search any vehicle having a usage history similar to that of the vehicle 20 (S240). If such a vehicle having the similar usage history is found, and the infection risk of such a vehicle is high, the external server 50 may send a command to the processor 32 to modify the communication frequency and/or the information to be transmitted to the external server 50 regardless of the current status of the infection risk (S250).

Optionally, the external server 50 may send a notification to the external user terminal 60. The notification may include, for example, an order for the disinfectant procedure and an updated reservation. The external server 50 may also send such a notification to a contractor providing a disinfectant service or a customer having the reservation via an email or a text message.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicant's contribution.

For example, the above-discussed steps may be stored in computer readable non-transitory storage medium as a series of operations or a program related to the operations that is executed by a computer system or other hardware capable of executing the program. In addition, the operations may be performed by a dedicated circuit implementing the program codes, a logic block or a program module executed by one or more processors, or the like. Moreover, all the steps shown in FIGS. 4 and 5 are implemented by the processor 32 on the vehicle terminal 30 in the above-discussed embodiments, all or some of these steps may be implemented by the external server 50.

Although the present disclosure is described mainly with respect to a vehicle managing system concerning the rental/shared car facility, the application of the present invention is not limited to such a car rental business. The present invention is also applicable to taxicab fleet management, ride-sharing fleet management, delivery truck fleet management, and other vehicle fleet management industries.

The actual scope of the protection sought is intended to be defined in the following claims when viewed in their proper perspective based on the prior art.

The invention claimed is:

1. A system for managing shared vehicles, the system comprising
    an acoustic event detector including an acoustic sensor for detecting an acoustic event in a compartment of a vehicle,
    a vehicle terminal electrically connected to the acoustic event detector, and
    an external server communicating with the vehicle terminal via a network,
    wherein at least one of the vehicle terminal and the external server comprises a processor, and
    the processor is configured to implement the steps of:
        extracting a respiratory disease symptom of a passenger in the vehicle from the detected acoustic event;
        assessing the respiratory disease symptom of the passenger to generate infection risk information associated with an infection risk of a next passenger expected to ride the vehicle; and
        transmitting the infection risk information to an external user terminal via the network.

2. The system according to claim 1, further comprising a position detector for detecting a current position of the vehicle,
    wherein the processor is further configured to implement the step of:
        obtaining at least one of environmental information around the vehicle and infection risk information from a neighboring vehicle via the network, and
    the step of assessing the respiratory disease of the passenger is implemented also on the basis of the at least one of environmental information around the vehicle and infection risk information from a neighboring vehicle.

3. The system according to claim 1, wherein the processor is further configured to implement the step of:
    modifying at least one of a communication frequency and information to be transmitted to the external server.

4. The system according to claim 1, further comprising an air cleaner in the vehicle,
    wherein the processor is further configured to implement the step of:
        controlling the air cleaner on the basis of a frequency of occurrence of the respiratory disease symptom.

5. The system according to claim 1, wherein the processor is further configured to implement the steps of:
    generating vehicle compartment contamination information indicating a necessity of a disinfectant procedure prior to a next use of the vehicle based on the infection risk information, and
    transmitting the vehicle compartment contamination information to the external user terminal via the network.

6. The system according to claim 5, wherein the external server comprises a database storing reservation information and status information of the shared vehicles, and modifies the status information of the vehicle to reflect the vehicle compartment contamination information.

7. The system according to claim 6, wherein when the vehicle compartment contamination information indicates that the disinfectant procedure is needed and the reservation information indicates that the vehicle has a reservation, the external server searches another available vehicle and assigns the available vehicle to the reservation.

8. The system according to claim 6, wherein the vehicle compartment contamination information is updated after the disinfectant procedure is completed so as to indicate that the vehicle is clean.

9. The system according to claim 1, wherein the external server searches a potentially contaminated vehicle having a usage history similar to that of the vehicle determined as high infection risk, and modifies at least one of a communication frequency and information to be transmitted to the external server.

10. A method for managing shared vehicles, the method comprising the steps of:
   detecting an acoustic event in a compartment of a vehicle;
   extracting a respiratory disease symptom of a passenger in the vehicle from the detected acoustic event;
   assessing the respiratory disease symptom of the passenger to generate infection risk information associated with an infection risk of a next passenger expected to ride the vehicle; and
   transmitting the infection risk information to an external user terminal via a network.

11. The method according to claim 10, further comprising the steps of:
   detecting a current position of the vehicle; and
   obtaining at least one of environmental information around the vehicle and infection risk information from a neighboring vehicle via the network,
   wherein the step of assessing the respiratory disease of the passenger is implemented also on the basis of the at least one of environmental information around the vehicle and infection risk information from a neighboring vehicle.

12. The method according to claim 10, further comprising the step of:
   modifying at least one of a communication frequency and information to be transmitted to an external server.

13. The method according to claim 10, further comprising the step of:
   controlling an air cleaner in the vehicle on the basis of a frequency of occurrence of the respiratory disease symptom.

14. The method according to claim 10, further comprising the step of:
   acquiring biological information of the passenger on the basis of a frequency of occurrence of the respiratory disease symptom.

15. The method according to claim 10, further comprising the steps of:
   generating vehicle compartment contamination information indicating a necessity of a disinfectant procedure prior to a next use of the vehicle based on the infection risk information; and
   transmitting the vehicle compartment contamination information to the external user terminal via the network.

16. The method according to claim 15, further comprising the steps of:
   accessing a database storing reservation information and status information of the shared vehicles; and
   modifying the status information of the vehicle to reflect the vehicle compartment contamination information.

17. The method according to claim 16, further comprising the step of:
   when the vehicle compartment contamination information indicates that the disinfectant procedure is needed and the reservation information indicates that the vehicle has a reservation, searching another available vehicle and assigns the available vehicle to the reservation.

18. The method according to claim 16, further comprising the step of:
   updating the vehicle compartment contamination information after the disinfectant procedure is completed so as to indicate that the vehicle is clean.

19. The method according to claim 10, further comprising the step of:
   searching a potentially contaminated vehicle having a usage history similar to that of the vehicle determined as high infection risk, and modifying at least one of a communication frequency and information to be transmitted to the external server.

\* \* \* \* \*